US009561276B2

(12) United States Patent
Lundahl

(10) Patent No.: US 9,561,276 B2
(45) **Date of Patent: *Feb. 7, 2017**

(54) METHOD OF TREATING ONYCHOMYCOSIS

(71) Applicant: DUSA PHARMACEUTICALS, INC., Wilmington, MA (US)

(72) Inventor: Scott Lundahl, Wilmington, MA (US)

(73) Assignee: DUSA PHARMACEUTICALS, INC., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/092,739

(22) Filed: Apr. 7, 2016

(65) Prior Publication Data

US 2016/0220674 A1 Aug. 4, 2016

Related U.S. Application Data

(63) Continuation of application No. 13/965,276, filed on Aug. 13, 2013, now Pat. No. 9,339,540.

(60) Provisional application No. 61/683,758, filed on Aug. 16, 2012.

(51) Int. Cl.

| | |
|---|---|
| ***A61N 5/06*** | (2006.01) |
| ***A61N 1/30*** | (2006.01) |
| ***A61K 41/00*** | (2006.01) |
| ***A61K 31/197*** | (2006.01) |

(52) U.S. Cl.

CPC ......... *A61K 41/0061* (2013.01); *A61K 31/197* (2013.01); *A61N 5/062* (2013.01); *A61N 2005/0663* (2013.01)

(58) Field of Classification Search

CPC ............................ A61N 5/062; A61K 41/0061

USPC .............................................. 607/88; 604/20

See application file for complete search history.

(56) References Cited

U.S. PATENT DOCUMENTS

| | | | |
|---|---|---|---|
| 5,955,490 A | 9/1999 | Kennedy et al. | |
| 6,710,066 B2 | 3/2004 | Kennedy et al. | |
| 6,897,238 B2 | 5/2005 | Anderson | |
| 7,033,381 B1 | 4/2006 | Larsen | |
| 9,339,540 B2 * | 5/2016 | Lundahl ............. | A61K 41/0061 |
| 2004/0110818 A1 | 6/2004 | Kennedy et al. | |
| 2006/0258635 A1 | 11/2006 | Smijs | |
| 2009/0099459 A1 | 4/2009 | Svanberg | |
| 2012/0058199 A1 | 3/2012 | Buthe et al. | |

OTHER PUBLICATIONS

Kamps, et al. "Antifungal effect of 5-aminolevulinic acid PDT in Trichophyton rubrum." Mycoses, 48, 101-107, Feb. 11, 2004.

Fitzpatrick and Freedberg, "Onychomycosis." Dermatology in General Medicine. vol. 2, Chapter 205, pp. 2001-2003, May 23, 2003.

Tosti, et al. "Biology of Nails." Fitzpatrick's Dermatology in General Medicine. Chapter 13, pp. 159-163, 2003.

Donnelly, et al. "Bioadhesive patch-based delivery of 5-aminolevulinic acid to the nail for photodynamic therapy of onychomycosis." Journal of Controlled Release 103 (2005) 381-392.

Pottier, et al. "Non-Invasive Technique for Obtaining Fluorescence Excitation and Emission Spectra In Vivo." Photochemistry and Photobiology, vol. 44, No. 5, pp. 679-687 (1986).

"Onychomycosis." Dermatology in General Medicine. vol. 2, Chapter 205, pp. 2001-2003.

International Search Report and Written Opinion for PCT/US13/54618 dated Jan. 3, 2014.

Watanabe et al., "Successful treatment of toenail onychomycosis with photodynamic therapy", Arch. Dermatol., 2008, 144(1), 19-21.

Piraccini et al., "Photodynamic therapy of onychomycosis caused by Trichophyton rubrum" J. Am. Acad. Dermatol., 2008, 59(5S), S75-76.

Gilaberte et al., "Treatment of refractory fingernail onychomycosis caused by nondermatophyte molds with methylaminolevulinate photodynamic therapy" J. Am. Acad. Dermatol., 2011, 65(3), 669-671.

Sotiriou et al., "Photodynamic therapy for distal and lateral subungual toenail onychomycosis caused by Trichophyton rubrum: Preliminary results of a single-centre open trial", Acta Derm. Venereol., 2010, 90(2), 216-217.

* cited by examiner

*Primary Examiner* — Lynsey Crandall
*Assistant Examiner* — Sebastian X Lukjan
(74) *Attorney, Agent, or Firm* — Matthew S. Gibson; Reed Smith LLP

(57) ABSTRACT

This application is directed to a method of treating onychomycosis by applying a phototherapeutic agent to a nail structure, waiting for a period of at least three days, and exposing the nail to light that causes an activation reaction. The phototherapeutic agent may be amino levulinic acid, alkylated derivatives of ALA, and their pharmaceutically acceptable salts.

11 Claims, No Drawings

METHOD OF TREATING ONYCHOMYCOSIS

RELATED APPLICATION

This application is a continuation of U.S. patent application Ser. No. 13/965,276, entitled METHOD OF TREATING ONYCHOMYCOSIS, filed Aug. 13, 2013 which claims priority of U.S. Patent Application Ser. No. 61/683,758, filed Aug. 16, 2012, the entire disclosure of which is hereby incorporated by reference as if being set forth in its entirety herein.

FIELD OF THE INVENTION

This invention relates to the treatment of disorders of the fingernail and toenail, known as onychomycosis.

BACKGROUND OF THE INVENTION

Nails are unique structures found on the fingers and toes. The nail apparatus consists of a nail plate and its associated soft tissue (the proximal nail fold, the matrix, the nail bed, and the hyponychium). In common lay usage the terms "fingernail" and "toenail" refer to the nail plate.

The nail plate is a unique skin structure. It consists mostly of highly filamentous proteins, known as keratin, embedded in an amorphous matrix. The nail plate differs from ordinary skin in many ways. Besides being much harder than ordinary skin, the nail plate also has a much lower lipid content, higher keratin content, more disulfide bonds and a much lower ability to absorb water. Because of the unique structure of nails, they present unique problems for the clinician who treats their disorders.

Onychomycosis is a frequently occurring disorder of the nails. It is caused by an infection of the nail plate and associated structures by fungi or yeasts. Most often, onychomycosis is caused by an infection of dermatophyte fungi of the genus *Tinea*. Onychomycosis results in a thickening and discoloration of the nails which can become breakable.

Onychomycosis is rarely, if ever, life threatening. It can be painful and is usually very unsightly and the cause of much embarrassment for the patient, especially when the fingernails are involved.

There are number of treatments for onychomycosis, none of which are highly effective.

A ciclopirox 8% nail lacquer (similar to nail polish) is sometimes used to treat onychomycosis. Sold under the brand Penlac, this product must be applied to the affected nails every day for almost a year. It results in complete clinical and mycological clearance in less than a quarter of cases.

Oral terbinafine hydrochloride is sold under the brand Lamisil and is used to treat onychomycosis. Terbinafine must be taken every day for three months in order to have success in treating onychomycosis of the toenail. Because it is administered orally, terbinafine therapy for onychomycosis is subject to a variety of adverse events unrelated to the treatment site, including gastrointestinal disorders, rashes, disruption of the sense of taste, and liver disorders. A complete course of treatment with terbinafine results in complete clearance in only a minority of cases.

In the many cases that are not responsive to topical or systemic drug therapy, the only remaining treatment for onychomycosis is the surgical or chemical removal of the nail plate which exposes the nail bed. Topical antifungals are then applied to the exposed nail bed while the nail plate is allowed to regrow, a process which takes about a year in the case of toenails.

Photodynamic therapy (PDT) is an established therapeutic method for certain disorders. PDT is characterized by the use of (1) a phototherapeutic agent and (2) light. The phototherapeutic agent is applied or provided to the tissue or organ of interest. The light is used to cause a photo-reaction (such as photoexcitation) in either the phototherapeutic agent, or in a metabolite of the phototherapeutic agent, or in a compound produced in response to the presence of the phototherapeutic agent (the activation reaction). This reaction results in a therapeutic effect.

Early phototherapeutic agents included porphyrins such as hematoporphyrin IX, hematoporphyrin derivative, or other such molecules, including Photofrin II.

The pioneering work of Kennedy & Pottier resulted in the discovery of the use of aminolevulinic acid (ALA) as a phototherapeutic agent. ALA is a precursor to a naturally occurring molecule—protoporphyrin IX. Exposing skin to light activates protoporphyrin IX in the skin. That is, the light excites or causes a reaction in the protoporphyrin IX molecule that results in the formation of reactive free radicals. Naturally occurring protoporphyrin IX can be activated by exposure to light, but occurs in quantities too small to cause any serious effect in normal tissue. By administering exogenous ALA, cells and tissues can be caused to produce greatly increased amounts of protoporphyrin IX. The resulting high concentrations of protoporphyrin IX can result in the generation of fatal quantifies of free radicals in the target cells/tissue when protoporphyrin IX is activated by exposure to light.

Kennedy & Pottier found that ALA-induced production of protoporphyrin IX made it possible to use PDT in the treatment of several disorders of metabolically active tissues. This technology has been used in the successful commercial product Levulan®, produced by Dusa Pharmaceuticals, and which has been approved by the U.S. FDA for the treatment of actinic keratoses.

Kennedy and his co-workers believed that ALA-based PDT could be used to treat acne, although they did not report any clinical resolution of acne by this method. See, U.S. Pat. No. 5,955,490. Also, they reported that the ability of light to specifically excite protoporphyrin IX in acne lesions disappeared within 24 hours.

Other workers in this field tried to employ ALA-based PDT in the treatment of acne. See, U.S. Pat. No. 6,897,238 to Anderson. Anderson used ALA based PDT to treat acne in a small group of patients and taught that light must be applied to the skin within one to 12 hours after application of ALA to the skin containing acne lesions, preferably about three hours after application of the ALA.

Anderson's use of a 1 to 12 hour waiting period, and preferably a three hour waiting period between ALA application and exposure to light was consistent with what was by then the generally accepted timeline of ALA metabolism and protoporphyrin IX production. Research by Kennedy & Pottier showed that ALA was metabolized in mouse skin to result in peak protoporphyrin IX concentration in about six hours, with protoporphyrin levels returning to near pretreatment baseline in about 18 hours. Pottier et al, *Photochemistry and Photobiology*, Vol. 44, No. 5, pp. 679-87 (1986).

ALA-based PDT was thought to have an ability to treat dermatophytic infections. Kennedy and Pottier reported the use of PLA-based PDT to treat onychomycosis of the toenail in U.S. Pat. No. 6,710,066. ALA was applied to the nail and the nail was exposed to photoactivating light four hours later. While they reported success in resolving the fungal infection, they also reported that ALA-based PDT caused redness and edema (swelling). Subsequent experience with this technique has shown that the edema caused by ALA-based PDT treatment of onychomycosis can be painful and severe. In some cases the swelling is so great that it restricts blood flow to the toe causing gangrene, which requires amputation of the toe. Lowering the dosage of ALA to avoid dangerous swelling of the toe and restriction of the blood flow results in the loss of effectiveness of the treatment.

There remains a great need for a highly effective and safe treatment of onychomycosis.

SUMMARY OF THE INVENTION

It has been discovered that ALA based PDT can be used to treat onychomycosis in a safe and effective manner. In the treatment method of the current invention, there is an extended period of delay or incubation between the time that ALA is applied to the affected region and the time that a photoactivating light is applied. This incubation period is from three to thirty days, preferably about ten days.

The treatment method of the present invention results in resolution of the fungal infection without dangerous side effects such as painful or life threatening edema.

DETAILED DESCRIPTION OF THE INVENTION

It has been discovered that the fungi that cause onychomycosis metabolize ALA to a photoactivatable compound differently than is the case with skin and skin lesions. Consequently, fungal metabolism of ALA results in therapeutic concentrations of photoactivable compounds three to thirty days after application of ALA to the oncychomycotic nail. This enables the employment of a significantly longer delay between application of ALA and the exposure to photoactivating light than had been thought possible. This delay allows PPIX levels in the surrounding toe or finger tissues to drop, thereby eliminating the risk that those tissues will be susceptible to painful swelling that can result in a dangerous restriction of blood flow to the toe or finger.

A delay of three days is often sufficient to reduce the risk of dangerous and/or painful swelling in the surrounding tissues while allowing effective treatment of the fungal infection of the nail. A delay of five days is further protective, and a delay of 10 days is further preferred. A delay of more than 20 days sometimes is less desirable, and the delay should be no longer than 30 days.

Derivatives of ALA, including alkylated derivatives of ALA, can also be used in the treatment method of this invention. These include $C_1$ to $C_8$ alkyl derivatives of ALA such as methyl ALA and hexyl ALA.

Topical formulations suitable for use in ALA-based PDT are well known in the art. These include ALA and its pharmaceutically acceptable salts, such as ALA hydrochloride and sodium ALA. Any topical vehicle that delivers ALA to the nail so that it can be taken up by the nail can be used. Levulan® ALA is a formulation that is commercially available and suited to use in this invention.

The concentration of ALA in the topical formulation can range from 1 to 30 percent. Concentrations within this range can be selected on the basis of the volume of the formulation to be applied, the size of the affected nail, the extent of the infection, and other clinical factors well known to practitioners, and well within the scope of good clinical judgment. Concentrations in the range of 5 to 20 percent are most useful, within 20 percent ALA being particularly useful.

The ALA can be applied to the nail by any of the conventional application techniques known in the art, such as swabs, brushes, cotton balls, gauze pads or the like. The Kerastick® applicator sold by DUSA Pharmaceuticals can also be used.

Light sources suitable for use in ALA-based PDT are also well known and generally available. The wavelengths of light that are capable of penetrating the nail and exciting the protoporphyrin IX molecule are well known to those skilled in the art. Devices capable of providing such light are also readily available. These include the BLU-U® illuminator, sold by DUSA Pharmaceuticals, and the Sciencetech (London, Ontario, Canada) Model 7500 PDTI (Photodynamic Therapy Illuminator), which emits red light in the 600-650 nm wavelength range.

Example 1

A 5 percent ALA solution was prepared by dilution of 20 percent ALA Topical Solution (Levulan® Kerastick® (aminolevulinic acid HCl) for Topical Solution, 20%). The ALA solution was then applied to a healthy volunteer suffering from mild to moderate onychomycosis involving the hallux (proximal or big toe) toenail and the second toenail of the left foot. The ALA solution was applied liberally to the nail surface and the periungual skin areas. The entire toe was wrapped in an occlusive dressing (Tegaderm®) for 12 hours. Twenty-four hours post ALA application, the treated area was examined for porphryin fluorescence using a long wave UV light (Wood's Light) as an excitation source.

Characteristic red fluorescence was noted to be present on both treated toes. Moderate to intense fluorescence presenting in a uniform pattern extended beyond the nail plate and infection into the periungual skin areas indicating the presence of high levels of porphyrin compounds in these areas. Only faint fluorescence was noted in the toenails themselves.

The subject was instructed to avoid light exposure to the treated toes. Fluorescence evaluation was performed again 10 days post ALA application. At this evaluation, bright red fluorescence was noted in the nail plates and infected areas of both treated toes whereas no characteristic fluorescence could be detected in the non-infected periungual skin areas.

The subject was then treated with 100 Joules/$cm^2$ of red light using the Sciencetech 7500 illuminator, causing an activation reaction.

The subject noted only mild tingling and slight stinging in the proximal toe and little to no sensation in the second toe during light treatment. A slight sensation of warmth was also noted in all areas exposed to the red light, most probably do to a slight heating effect from the light itself.

The subject was again instructed to avoid light exposure to the treated toes. Follow up evaluations were performed 5 and 20 days post light treatment (15 and 30 days post ALA application). At the 5 day post light evaluation the proximal toe exhibited only slight edema in the area around the nail plate, and mild redness of the nail bed itself. The second toe exhibited only slight redness in the nail bed. Fluorescence evaluation again showed characteristic fluorescence in the nail plates, however, the intensity appeared diminished compared to the pre red light 10 day evaluation. An evaluation at 20 days after exposure to the activating red light showed that both treated toes appeared normal, although slight fluorescence was still present in the nail plates on evaluation.

The treated nails then grew out, clear of all discoloration, thickening or fungal infection. The subject noted no adverse effects associated with the treatment.

The invention claimed is:

1. A method of treating onychomycosis comprising the steps of:

applying aminolevulinic acid (ALA) or its pharmaceutically acceptable salt to a nail structure of a subject, wherein the subject has onychomycosis of the nail structure;

allowing a waiting period of between 5 days and 30 days after applying ALA; and exposing the nail to a light after the waiting period, wherein the light causes an activation reaction.

2. The method of claim 1, wherein the waiting period is at least 10 days.

3. The method of claim 1, wherein the waiting period is at least 20 days.

4. The method of claim 1, wherein the waiting period is between 10 and 20 days.

5. The method of claim 1, wherein the waiting period is between 10 and 30 days.

6. The method of claim 1, wherein the waiting period is between 20 and 30 days.

7. The method of claim 1, wherein the light emits red light in the 600-650 nm wavelength range.

8. A method of treating onychomycosis comprising the following steps:

applying a solution to a nail structure of a subject, wherein the solution comprises aminolevulinic acid (ALA) or its pharmaceutically acceptable salt at a concentration of 5%-20% of the volume of the solution, and wherein the subject has onychomycosis of the nail structure;

allowing a waiting period of between 10 days and 30 days after applying ALA; and exposing the nail to a light after the waiting period, wherein the light emits red light in the 600-650 nm wavelength range.

9. A method of treating onychomycosis comprising the following steps:

applying a solution to a nail structure of a subject, wherein the solution comprises aminolevulinic acid (ALA) or its pharmaceutically acceptable salt at a concentration of 5%-20% of the volume of the solution, and wherein the subject has onychomycosis of the nail structure;

allowing a waiting period of between 5 days and 30 days after applying ALA; and exposing the nail to a light after the waiting period, wherein the light causes an activation reaction.

10. The method of claim 9, wherein the light emits red light in the 600-650 nm wavelength range.

11. The method of claim 9, wherein the waiting period is at least 10 days.

* * * * *